United States Patent [19]

Smith et al.

[11] Patent Number: 4,736,056

[45] Date of Patent: Apr. 5, 1988

[54] PROCESS FOR THE PRODUCTION OF MALONIC ACID DERIVATIVE COMPOUNDS

[76] Inventors: Oliver W. Smith, 4608 Oak Park Rd., Raleigh, N.C. 27612; Russell J. Outcalt, 107 Coatbridge Cir., Cary, N.C. 27511

[21] Appl. No.: 941,863

[22] Filed: Dec. 15, 1986

[51] Int. Cl.$^4$ ............................................. C07C 101/44
[52] U.S. Cl. ......................................... 560/43; 560/16; 558/252; 558/254; 558/256; 558/235; 558/234; 558/230; 562/455; 564/74; 564/162; 564/163; 564/167; 548/549
[58] Field of Search ............... 560/43, 16; 558/252, 558/254, 256

[56] References Cited

U.S. PATENT DOCUMENTS

| 4,252,739 | 2/1981 | Fayter, Jr. et al. | 260/465 K |
| 4,307,034 | 12/1981 | Nakayama et al. | 260/465 R |
| 4,556,409 | 12/1985 | Fayter, Jr. et al. | 71/76 |

OTHER PUBLICATIONS

Dox A. et al., J. Am. Chem. Soc. 43, 2097 (1921).
White, D. A. Synthetic Communications 7(8) 559–568, (1977).
Zefirov, N. S. et al., Zh. Org. Khim. 19 474–480 (1983).
Gosselck, J. et al., Angew. Chem. Internat. Edit., vol. 7, No. 6, pp. 456–457 (1968).
Ohishi, J., Communications, pp. 690–691 (Sep. 1980).
Gosselck, J. et al., Tetrahedron Letters, No. 8, pp. 995–998 (1968).
Conners, T. A. et al., J. Chem. Soc., pp. 2129 (1960).
Harsanyi, K. et al., Chemical Abstracts, vol. 102, pp. 588–589 (1985).
Sumitani, M., Chemical Abstracts, vol. 90, pp. 564 (1979).
Singh, R. K. et al., J. Org. Chem., vol. 40, No. 20, pp. 2969–2970 (1975).

*Primary Examiner*—Paul J. Killos

[57] ABSTRACT

This invention relates to a process for preparing a malonic acid derivative compound of formula (i) depicted herein in high yield and high purity by reacting a malonic acid derivative compound of formula (ii) depicted herein with an alkylating agent of formula (iii) depicted herein in the presence of a solvent and a base.

33 Claims, No Drawings

PROCESS FOR THE PRODUCTION OF MALONIC ACID DERIVATIVE COMPOUNDS

BRIEF SUMMARY OF THE INVENTION

1. Technical Field

This invention relates to a process for the preparation of malonic acid derivative compounds in high purity and high yield.

2. Background of the Invention

The cycloalkylation reaction of a dialkyl malonate such as dimethyl malonate with an alkylating agent such as 1,2-dibromoethane in the presence of a solvent and a base is known in the art. See, for example, Dox, A. and Yoder, L., J. Am. Chem. Soc., 43, 2097 (1921); White, D. A., Synthetic Communications, 7(8), 559–568 (1977); Zefirov, N. S. et al., Zh. Org. Khim., 19, 474–480 (1983); Harsangi, K. et al., Hung. Teljes Hu, 32, 794 (1984); and U.S. Pat. No. 4,307,034.

U.S. Pat. No. 4,252,739 discloses a process for the preparation of vinylcyclopropane derivatives which involves reacting an alkylating agent and an activated methylene compound using an onium catalyst in the presence of an alkali metal compound and water. Example 38 of this patent describes the reaction of acetoacetanilide with trans-1,4-dichlorobut-2-ene in the presence of methylene chloride and potassium hydroxide to give the vinylcyclopropane derivative of acetoacetanilide.

DISCLOSURE OF THE INVENTION

This invention relates to a process for preparing a compound of formula (i)

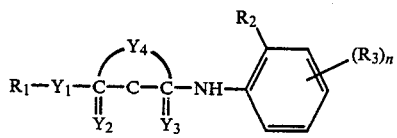  (i)

which comprises reacting a compound of formula (ii)

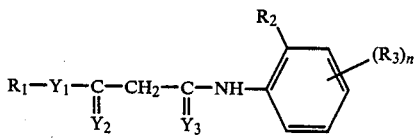  (ii)

with a compound of formula (iii)

-Y$_4$-X$_2$    (iii)

in the presence of a solvent and a base; wherein R$_1$, R$_2$, R$_3$, n, Y$_1$, Y$_2$, Y$_3$, Y$_4$, X$_1$, and X$_2$ are as defined hereinafter.

DETAILED DESCRIPTION

As indicated above, this invention relates to a process for the production of malonic acid derivative compounds. More particularly, this invention involves a process for preparing a compound of formula (i)

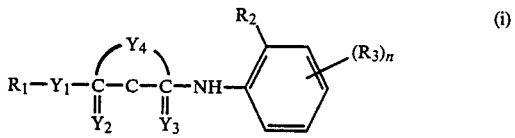

which comprises reacting a compound of formula (ii)

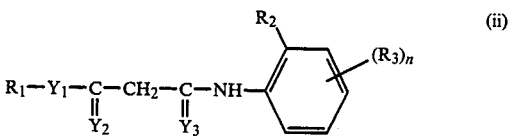

with a compound of formula (iii)

in the presence of a solvent and a base;
wherein:

R$_1$ is alkyl, hydroxyalkyl alkoxyalkyl, alkoxycarbonylalkyl, alkylaminoalkyl, dialkylaminoalkyl, aryl, mercaptoalkyl, alkylthioalkyl, arylthioalkyl, aryloxyalkyl, alkylsulfonylalkyl, alkylsulfinylalkyl, acylalkyl, aroylalkyl, dialkoxyphosphinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalkylene)alkyl, cyanoalkyl, nitroalkyl, alkylideneamino, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, aminosulfonylalkyl, alkylaminosulfonylalkyl or dialkylaminosulfonylalkyl;

R$_2$ and R$_3$ are the same or different and are halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonylamino, acyloxy or alkenyl.

n is a value of from 0 to 4;

Y$_1$ is O, S or N(alkyl);

Y$_2$ and Y$_3$ are independently oxygen or sulfur;

Y$_4$ is a substituted or unsubstituted branched or straight chain containing two or more carbon atoms or heteroatoms in any combination in which the permissible substituents are the same or different and are one or more halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonylamino, acyloxy or alkenyl, with the proviso that X$_1$ and X$_2$ are not directly bonded to a heteroatom; and X$_1$ and X$_2$ are independently nucleofuge groups having sufficient leaving capability to permit the reaction of a compound or formula (iii) with a compound of formula (ii) to form a compound of formula (i).

The malonic acid derivative compounds of formula (i) which are prepared by the process of this invention are useful for retarding plant growth and increasing crop yield. These malonic acid derivative compounds can also be used in combination with an ethylene response or ethylene-type response inducing agent such as ethephon for inducing synergistic plant growth regulator responses.

Preferred malonic acid derivative compounds of formula (i) which can be prepared by the process of this invention have the following formulae:

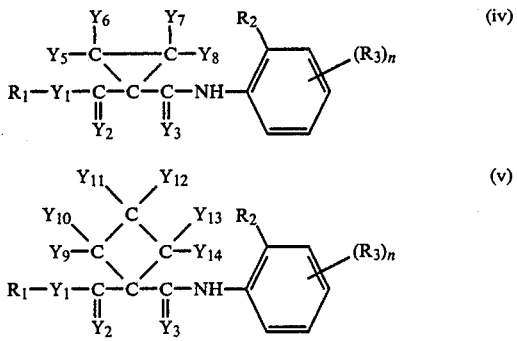

wherein $R_1$, $R_2$, $R_3$, n, $Y_1$, $Y_2$ and $Y_3$ are as defined hereinabove and $Y_5$, $Y_6$, $Y_7$, $Y_8$, $Y_9$, $Y_{10}$, $Y_{11}$, $Y_{12}$, $Y_{13}$ and $Y_{14}$ are independently hydrogen, halogen or alkyl.

Illustrative of malonic acid derivative compounds of formula (i) and acid and salt derivatives thereof which can be prepared by the process of this invention include the following:

ethyl 1-(4-bromo-2-methylphenylaminocarbonyl)cyclopropanecarboxylate;
1-(4-bromo-2-methylphenylaminocarbonyl)cyclopropanecarboxylic acid;
ethyl 1-(2,4-dichlorophenylaminocarbonyl)cyclopropanecarboxylate;
ethyl 1-(4-methoxy-2-methylphenylaminocarbonyl)cyclopropanecarboxylate;
ethyl 1-(4-nitro-2-methylphenylaminocarbonyl)cyclopropanecarboxylate;
ethyl 1-(4-chloro-2-fluorophenylaminocarbonyl)cyclopropanecarboxylate;
methyl 1-(4-bromo-2-methylphenylaminocarbonyl)cyclopropanecarboxylate;
1-(2,4-dichlorophenylaminocarbonyl)cyclopropanecarboxylic acid;
ethyl 1-(4-bromo-2-fluorophenylaminocarbonyl)cyclopropanecarboxylate;
ethyl 1-(4,5-dichloro-2-methylphenylaminocarbonyl)cyclopropanecarboxylate;
methyl 1-(2,4,5-trichlorophenylaminocarbonyl)cyclopropanecarboxylate;
ethyl 1-(4-bromo-5-chloro-2-methylphenylaminocarbonyl)cyclopropanecarboxylate;
ethyl 1-(4-bromo-2-chlorophenylaminocarbonyl)cyclopropanecarboxylate;
methyl 1-(2-chloro-4-trifluoromethylphenylaminocarbonyl)cyclopropanecarboxylate;
benzyl 1-(4-bromo-2-methylphenylaminocarbonyl)cyclopropanecarboxylate;
propargyl 1-(4-bromo-2-methylphenylaminocarbonyl)cyclopropanecarboxylate;
ethyl 1-(4-bromo-2-methylphenylaminocarbonyl)cyclobutanecarboxylate;
sodium 1-(4-bromo-2-methylphenylaminocarbonyl)cyclopropanecarboxylate;
potassium 1-(4-bromo-2-methylphenylaminocarbonyl)cyclopropanecarboxylate;
1-(4-bromo-2-methylphenylaminocarbonyl)cyclobutanecarboxylic acid;
ethyl 1-(2,4-dichlorophenylaminocarbonyl)cyclobutanecarboxylate; and
1-(2,4-dichlorophenylaminocarbonyl)cyclobutanecarboxylic acid.

The malonic acid derivative compounds of formula (ii) used as reactants in the process of this invention are known compounds which can be prepared by conventional methods. It is important that the aniline ring of the malonic acid derivative compounds of formula (ii) be ortho substituted in order to obtain malonic acid derivative compounds of formula (i) in high yield and high purity. Product yields ranging from 70 percent and higher and product purities in excess of 90 percent can be obtained by the process of this invention. In the absence of such an ortho substituent, N-alkylation occurs causing the formation of undesired byproducts such as various lactams and imino ethers. Additionally, the presence of an ortho substituent on the aniline ring typically provides for faster reaction periods than corresponding non-ortho substituted analogues.

Illustrative of malonic acid derivative compounds of formula (ii) which can be used as reactants in the process of this invention include the following:
ethyl 3-[(4-bromo-2-methylphenyl)amino]-3-oxopropanoate;
ethyl 3-[(2,4-dichlorophenyl)amino]-3-oxopropanoate;
ethyl 3-[(4-methoxy-2-methylphenyl)amino]-3-oxopropanoate;
ethyl 3-[(4-nitro-2-methylphenyl)amino]-3-oxopropanoate;
ethyl 3-[(4-chloro-2-fluorophenyl)amino]-3-oxopropanoate;
methyl 3-[(4-bromo-2-methylphenyl)amino]-3-oxopropanoate;
ethyl 3-[(4-bromo-2-fluorophenyl)amino]-3-oxopropanoate;
ethyl 3-[(4,5-dichloro-2-methylphenyl)amino]-3-oxopropanoate;
methyl 3-[(2,4,5-trichlorophenyl)amino]-3-oxopropanoate;
ethyl 3-[(4-bromo-5-chloro-2-methylphenyl)amino]-3-oxopropanoate;
ethyl 3-[(4-bromo-2-chlorophenyl)amino]-3-oxopropanoate;
methyl 3-[(2-chloro-4-trifluoromethylphenyl)amino]-3-oxopropanoate;
benzyl 3-[(4-bromo-2-methylphenyl)amino]-3-oxopropanoate; and
propargyl 3-[(4-bromo-2-methylphenyl)amino]-3-oxopropanoate.

The alkylating agents of formula (iii) used as reactants in the process of this invention are known compounds which can be prepared by conventional methods. As depicted by formula (iii), both $X_1$ and $X_2$ are independently nucleofuge groups having sufficient leaving capability to permit the reaction of a compound of formula (iii) with a compound of formula (ii) to form a compound of formula (i). Suitable nucleofuge groups encompassed within the definition of $X_1$ and $X_2$ include, for example, halogen, alkoxycarbonyloxy, haloalkylcarbonyloxy, polyhaloalkylcarbonyloxy, arylsulfonyloxy, alkylsulfonyloxy, haloalkylsulfonyloxy, polyhaloalkylsulfonyloxy, halosulfonyloxy, nitrooxy, dialkoxyphosphinyloxy, diaryloxyphosphinyloxy, aryloxy and the like, and also dialkylsulfonium, trialkylammonium and dialkyloxonium salts with suitable counterions and the like. Illustrative of alkylating agents of formula (iii) which can be used as reactants in the process of this invention include 1,2-dibromoethane, 1-bromo-2-chloroethane, 2-bromoethyl ethyl carbonate and the like. In the alkylating agents depicted by formula (iii), it is preferred that at least one of $X_1$ and $X_2$ is bromo or iodo or another nucleofuge group having comparable leaving capability.

The amount of the malonic acid derivative compound of formula (ii) and the alkylating agent of formula (iii) used in the process of this invention can vary over a wide range. In general, the molar ratio of the malonic acid derivative compound of formula (ii) to the alkylating agent of formula (iii) can range from about 0.25:1 to about 1.5:1. Preferably, an equimolar amount or slight excess of alkylating agent is employed to ensure that the malonic acid derivative compound of formula (ii) is completely reacted.

Various solvents can be used in the process of this invention. The preferred solvents are polar aprotic solvents such as dimethylformamide, dimethylsulfoxide, tetramethylenesulfone, dimethylacetamide, N-methyl pyrrolidinone, hexamethylphosphoric triamide, 3-methyl-2-oxazolidinone and the like. Other solvents such as acetonitrile, tetrahydrofuran, acetone, dioxane, diethyl ether, toluene, benzene, methanol, ethanol, 1,2-dibromoethane and the like may also be used in the process of this invention. The particular solvent used in the process of this invention is in general influenced by such factors as the amount and type of catalyst, if any, the amount and type of base and the like. The amount of solvent used in the process of this invention can vary over a wide range as practiced in the art, and is in general influenced by the amount of reactants and reaction conditions.

Various bases can be used in the process of this invention. The preferred bases are alkali metal carbonates such as potassium carbonate, sodium carbonate, cesium carbonate and the like which have a small particle size. Alkaline earth metal carbonates such as calcium carbonate and magnesium carbonate can also be used in the process of this invention. Other bases such as sodium hydride, potassium hydride, sodium amide, lithium diisopropylamide, lithium hexamethyldisilazide, sodium hydroxide, potassium hydroxide, sodium ethoxide, potassium t-butoxide, magnesium ethoxide, tertiary amines and the like may be used in the process of this invention. The particular base used as a solid in the process of this invention preferably has a small particle size, e.g., ranging from about 10 microns or less to about 1000 microns, which size contributes to accelerate the reaction rate. However, a base having macroscopic particle size can also be used in the process of this invention. The particular base is in general influenced by such factors as the amount and type of solvent, the amount and type of reactants and the like. The amount of base used in the process of this invention can vary over a wide range as practiced in the art, and is in general influenced by the amount of reactants and reaction conditions.

The reaction temperature is not narrowly critical and can be varied over a wide range. However, side reactions of the alkylating agent may occur at elevated temperatures in excess of about 80° C. The process of this invention is normally conducted at a temperature in the range of from about 20° C. to about 75° C., preferably from about 25° C. to about 50° C. For convenience, the reaction is usually conducted at ambient temperature.

Reaction pressures are not critical. The process of this invention can be conducted at either subatmospheric, atmospheric or superatmospheric pressure. For convenience, the reaction is usually conducted at atmospheric or autogenous pressure.

The reaction time period is not narrowly critical and can vary over a wide range. The process of this invention is effected over a period of time sufficient to produce the malonic acid derivative compound of formula (i). Generally, when operating under preferred reaction conditions, reaction times of from about 2 hours or less to about 12 hours are sufficient to complete the reaction of the malonic acid derivative compound of formula (ii) with the alkylating agent of formula (iii). Reaction time is influenced by the degree of mixing and the particle size of the base. Efficient mixing and small particle size of the base contribute to accelerate the reaction rate.

The process of this invention can be conducted under phase transfer conditions. Liquid-liquid phase transfer reactions can be conducted in a system containing water and an immiscible solvent such as toluene, benzene, dichloromethane, chloroform, ethyl acetate and the like in the presence of a phase transfer catalyst under similar reaction conditions as described above. Suitable phase transfer catalysts for the liquid-liquid phase transfer reaction include ammonium, phosphonium and sulfonium salts such as tetrabutylammonium bromide, tricaprylmethylammonium chloride, tributyldecylphosphonium bromide, triethylsulfonium iodide and the like. Other suitable catalysts are described, for example, in U.S. Pat. No. 4,252,739. Solid-liquid phase transfer reactions can be conducted in an organic solvent such as toluene, acetonitrile, dichloromethane, tetrahydrofuran, dioxane and the like in the presence of a crown ether catalyst or cryptate catalyst under similar reaction conditions as described above. Suitable crown ether and cryptate catalysts for the solid-liquid phase transfer reaction include 18-crown-6 ether, 15-crown-5 ether, dibenzo-18-crown-6 ether, dicyclohexyl-18-crown-6 ether, Kryptofix ®222 (4, 7, 13, 16, 21, 24-hexaoxa-1,10-diazabicyclo [8.8.8]hexacosane) and TDA-1 (tris[2-(2-methoxyethoxy)ethyl]amine). Additionally, quaternary ammonium salts such as tetrabutylammonium bromide and the like are suitable catalysts for solid-liquid phase transfer reactions.

The amount of catalyst which can be used in the phase transfer reactions is a catalytically effective amount and can vary over a wide range. Generally, the amount of catalyst employed can range from about 0.01 weight percent to about 10.0 weight percent or higher based on the total weight of the reactants.

The malonic acid derivative compounds of formula (i) can be further reacted using conventional procedures to prepare acid or salt deriviatives thereof in accordance with this invention. For example, the malonic acid derivative compound of formula (i) can be reacted with an alkali metal hydroxide, e.g., potassium hydroxide, sodium hydroxide and the like, to form an alkali metal salt derivative thereof which can be further reacted with an acid, e.g., mineral acids such as hydrochloric acid, sulfuric acid, perchloric acid and the like, to form an acid derivative thereof. This acid derivative can be reacted with ammonia or an amine, e.g., triethylamine, diisopropylamine and the like, to form an amine salt.

Other ingredients can optionally be employed in the process in this invention such as antifoaming agents and surfactants. Such antifoaming agents and surfactants are conventional materials known in the art. Suitable antifoaming agents include, for example, silicone antifoaming agents such as SAG 100 which is available from Union Carbide Corporation, Danbury, Conn. Suitable surfactants include, for example, conventional nonionic and anionic materials such as polyethylene glycols, sodium oleate, sulfates of higher fatty alcohols, aliphatic or aromatic sulfonates and the like. The amount of antifoaming agent and surfactant employed in the process of this invention can range from about 0.0001 weight percent or less to about 1.0 weight percent or greater (based on the weight of the entire reaction mass) for each ingredient.

The process of this invention can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressures. Means to introduce and/or adjust the quantity of reactants or ingredients introduced, either intermittently or continuously into the reaction zone during the course of the reaction can be conveniently utilized in the process especially to maintain the desired molar ratio of the reactants.

The process is preferably conducted in either glass lined, stainless steel or similar type reaction equipment. The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reaction mixtures can be employed. Mixing by vibration, shaking, stirring, rotation, oscillation, ultrasonic vibration or the like are all illustrative of the types of agitation means contemplated. Such means are available and well known to those skilled in the art.

The following numbered examples are illustrative of the process of this invention:

EXAMPLE A

Preparation of ethyl 3-[(4-bromo-2-methylphenyl)amino]-3-oxopropanoate

Into a 500 milliliter four-necked round-bottom reaction flask equipped with a mechanical stirrer, Dean-Stark trap/condenser, thermometer and heating mantle was added 320 grams (2.0 mol) of diethyl malonate and 37.2 grams (0.2 mol) of 4-bromo-2-methylaniline. The resulting mixture was heated at a temperature of 160° C. for a period of four hours and then cooled to a temperature of about 0° C. to form a precipitate. After filtering on a fritted glass funnel, the wet-cake was washed with heptane and air dried to give 37.6 grams (0.125 mol) of ethyl 3-[(4-bromo-2-methylphenyl)amino]-3-oxopropanoate. Liquid chromatographic analysis indicated 97 percent purity by comparison with an authenic sample of pure material. NMR analysis of the product indicated the following: $^1$H NMR (CDCl$_3$) δ9.52 (1H, bs), 8.02 (1H, d, J=9 Hz), 7.2–7.5 (2H, m), 4.30 (2H, q, J=7 Hz), 3.50 (2H, s), 2.30 (3H, s), 1.30 (3H, t, J=7 Hz).

EXAMPLE B

Preparation of ethyl 1-(4-bromophenylaminocarbonyl)cyclopropanecarboxylate

Into a 500 milliliter three-necked Morton flask equipped with a mechanical stirrer, thermometer and nitrogen inlet and outlet was added 38.1 grams (0.13 mol) of ethyl 3-[(4-bromophenyl)amino]-3-oxopropanoate, 45.9 grams (0.33 mol) of anhydrous potassium carbonate, 100 milliliters of anhydrous dimethylformamide and 11.6 milliliters (0.13 mol) of 1,2-dibromoethane. The resulting mixture was stirred at ambient temperature under a nitrogen atmosphere for a period of 9 days with slow consumption of ethyl 3-[(4-bromophenyl)amino]-3-oxopropanoate as monitored by high pressure liquid chromatographic analysis (reverse-phase C-18, 3:1 volume/volume acetonitrile-water eluent). An additional 0.6 milliliters (6.7 mmol) of 1,2-dibromoethane was added and stirring was continued for an additional 3 days. The reaction mixture was diluted with methylene chloride, filtered and the filtrate concentrated under reduced pressure. The filtrate was washed with a solution of 20 milliliters of glacial acetic acid in 150 milliliters of water and a solution of saturated aqueous sodium chloride. The solids which were separated by filtration were dissolved in water, acidified with acetic acid and extracted with methylene chloride (2×100 milliliters). These extracts were combined with the organic layer from the filtrate, dried over anhydrous magnesium sulfate and concentrated under reduced pressure. The residue was chromatographed on silica gel using initially a 3:1 volume/volume hexane-ethyl acetate eluent. Fractions containing polar products were then rechromatographed using 4:1 volume/volume toluene-ethyl acetate as the eluent to effect complete separation. Early fractions contained 23.09 grams (0.074 mol) of ethyl 1-(4-bromophenylaminocarbonyl)cyclopropanecarboxylate as a colorless solid having a melting point of 91.0° C.–92.0° C. The total yield was 56 percent. NMR analysis of the product indicated the following:

$^1$H NMR (CDCl$_3$) δ7.4–7.8 (4H, m), 4.30 (2H, q, J=7 Hz), 1.5–2.0 (4H, m), 1.30 (3H, t, J=7 Hz) ppm.

Intermediate fractions from the chromatography contained 1.46 grams (0.0035 mol) of N-(4-bromophenyl)-2-(2-bromoethyl)-2-carboethoxy-γ-butyrolactam as a tan amorphous solid having a melting point of 75.0° C.–77.5° C. NMR analysis indicated the following:

$^1$H NMR (CDCl$_3$) δ7.50 (4H, s), 4.22 (4H, q, J=7 Hz), 3.33–3.97 (4H, m), 2.05–3.00 (4H, m), 1.28 (3H, t, J=7 Hz) ppm.

The final fractions eluted contained 7.26 grams (0.023 mol) of N-(4-bromophenyl)-2-carboethoxy-γ-butyrolactam as a pale tan solid having a melting point of 60.0° C.–66.0° C. Recrystallization from hexane-ethyl acetate furnished 4.97 grams (0.016 mol) of colorless platelets having a melting point of 66.5° C.–68.0° C. NMR analysis indicated the following:

$^1$H NMR (CDCl$_3$) δ7.40–7.83 (4H, m), 4.33 (2H, q, J=7 Hz), 3.47–4.14 (3H, m), 2.22–2.80 (2H, m), 1.32 (3H, t, J=7 Hz) ppm.

EXAMPLE C

Preparation of ethyl 1-(4-methoxyphenylaminocarbonyl)cyclopropanecarboxylate In a manner similar to the procedure described in Example B except that a 100 milliliter three-necked Morton flask was used, 10.0 grams (42.0 mmol) of ethyl 3-[(4-methoxyphenyl)amino]-3-oxopropanoate, 14.54 grams (105.0 mmol) of anhydrous potassium carbonate, 30 milliliters of dimethylformamide and 7.9 grams (42.0 mmol) of 1,2-dibromoethane were reacted for a period of 12 days to give 5.74 grams (22.0 mol) of ethyl 1-(4-methoxyphenylaminocarbonyl)cyclopropanecarboxylate as a colorless solid having a melting point of 89.5° C.-91.0° C. The total yield was 56 percent. NMR analysis of the product indicated the following:

$^1$H NMR (CDCl$_3$) $\delta$11.07 (1H, bs), 7.62 (2H, d, J=9 Hz), 6.93 (2H, d, J=9 Hz), 4.23 (2H, q, J=7 Hz), 3.83 (3H, s), 1.4–2.1 (4H, m), 1.27 (3H, t, J=7 Hz) ppm.

The other fractions eluted contained 2.99 grams (11.4 mmol) of N-(4-methoxyphenyl)-2-carboethoxy-$\gamma$-butyrolactam as a colorless solid having a melting point of 66.0° C.-71.0° C. An analytical sample was prepared by low temperature recrystallization from methylene chloride-hexane having a melting point of 74.5° C.-75.5° C. NMR analysis indicated the following:

$^1$H NMR (CDCl$_3$) $\delta$7.62 (2H, d, J=9 Hz), 7.00 (2H, d, J=9 Hz), 4.32 (2H, q, J=7 Hz), 3.5–4.2 (3H, m), 3.85 (3H, s), 2.2–2.8 (2H, m), 1.30 (3H, t, J=7 Hz) ppm.

EXAMPLE D

Preparation of ethyl 1-(phenylaminocarbonyl)cyclopropanecarboxylate

In a manner similar to the procedure described in Example B except that a 100 milliliter three-necked Morton flask was used, 10.36 grams (50.0 mmol) of ethyl 3-[(phenyl)amino]-3-oxopropanoate, 18.95 grams (137.0 mmol) of anhydrous potassium carbonate, 30 milliliters of anhydrous dimethylformamide and 4.7 milliliters (55.0 mmol) of 1,2-dibromoethane were reacted for a period of 7 days to give, after chromatography on silica gel using a 3:1 volume/volume hexane-ethyl acetate eluent, 6.19 grams (27.0 mmol) of ethyl 1-(phenylaminocarbonyl)cyclopropanecarboxylate as a colorless solid having a melting point of 87.0° C.-89.0° C. The total yield was 55 percent. An analytical sample was prepared by recrystallization from hexane-ethyl acetate to give 5.44 grams (23.3 mmol) of ethyl 1-(phenylaminocarbonyl)cyclopropanecarboxylate as colorless needles having a melting point of 89.0° C.-90.0° C. NMR analysis of the product indicated the following:

$^1$H NMR (CDCl$_3$) $\delta$11.35 (1H, bs), 6.90–7.77 (5H, m), 4.17 (2H, q, J=7 Hz), 1.43–2.00 (4H, m), 1.23 (3H, t, J=7 Hz) ppm.

Other fractions eluted contained 0.47 grams (1.4 mmol) of N-phenyl-2-(2-bromoethyl)-2-carboethoxy-$\gamma$-butyrolactam as a colorless oil. NMR analysis indicated the following:

$^1$H NMR (CDCl$_3$) $\delta$7.0–8.0 (5H, m), 4.32 (2H, q, J=7 Hz), 3.37–4.60 (4H, m), 2.20–3.13 (4H, m), 1.32 (3H, t, J=7 Hz) ppm.

Other fractions eluted contained 2.80 grams (11.0 mmol) of N-phenyl-2-carboethoxy-$\gamma$-butyrolactam as a colorless solid. An analytical sample was prepared by recrystallization from hexane-ethyl acetate to give 1.83 grams (7.8 mmol) of N-phenyl-2-carboethoxy-$\gamma$-butyrolactam as colorless platelets having a melting point of 49.0° C.-50.0° C. NMR analysis indicated the following:

$^1$H NMR (CDCl$_3$) $\delta$7.00–7.77 (5H, m), 4.25 (2H, q, J=7 Hz), 3.48–4.10 (3H, m), 2.20–2.67 (2H, m), 1.32 (3H, t, J=7 Hz) ppm.

EXAMPLE E

Preparation of ethyl 1-(4-cyanophenylaminocarbonyl)cyclopropanecarboxylate

In a manner similar to the procedure described in Example B except that a 100 milliliter three-necked Morton flask was used, 10.0 grams (43.0 mmol) of ethyl 3-[(4-cyanophenyl)amino]-3-oxopropanoate, 14.8 grams (108.0 mmol) of anhydrous potassium carbonate, 40 milliliters of anhydrous dimethylformamide and 3.7 milliliters (43.0 mmol) of 1,2-dibromoethane were reacted for a period of 8 days to give 5.19 grams (20.0 mmol) of ethyl 1-(4-cyanophenylaminocarbonyl)cyclopropanecarboxylate as a colorless solid having a melting point of 132.0° C.-133.5° C. The total yield was 47 percent. An analytical sample was prepared by recrystallization from hexane-ethyl acetate having a melting point of 133.0° C.-134.0° C. NMR analysis of the product indicated the following:

$^1$H NMR (CDCl$_3$) $\delta$11.65 (1H, bs), 7.92 (2H, d, J=10 Hz), 7.67 (2H, d, J=10 Hz), 4.28 (2H, q, J=7 Hz), 1.5–2.1 (4H, m), 1.30 (3H, t, J=7 Hz) ppm.

Other fractions eluted contained 0.54 grams (1.48 mmol) of N-(4-cyanophenyl)-2-(2-bromoethyl)-2-carboethoxy-$\gamma$-butyrolactam as a pale yellow solid. Recrystallization from hexane furnished 0.53 grams (1.45 mmol) of N-(4-cyanophenyl)-2-(2-bromoethyl)-2-carboethoxy-$\gamma$-butyrolactam as colorless needles having a melting point of 112.0° C.-113.0° C. NMR analysis indicated the following:

$^1$H NMR (CDCl$_3$) $\delta$7.97 (2H, d, J=10 Hz), 7.73 (2H, d, J=10 Hz), 3.3–4.6 (4H, m with a 2H, q, J=7 Hz centered at 4.33), 2.1–3.2 (4H, m), 1.27 (3H, t, J=7 Hz) ppm.

Other fractions eluted contained 1.0 grams (3.9 mmol) of N-(4-cyanophenyl)-2-carboethoxy-$\gamma$-butyrolactam as a pale yellow amorphous solid having a melting point of 61° C.-65° C. NMR analysis indicated the following:

$^1$H NMR (CDCl$_3$) $\delta$7.5–8.2 (4H, m), 3.5–4.6 (3H, m with a 2H, q, J=7 Hz centered at 4.37), 2.3–2.9 (2H, m), 1.30 (3H, t, J=7 Hz)ppm.

EXAMPLE F

Preparation of ethyl 1-(4-nitrophenylaminocarbonyl)cyclopropanecarboxylate

In a manner similar to the procedure described in Example B except that a 100 milliliter three-necked Morton flask was used, 10.0 grams (39.6 mmol) of ethyl 3-[(4-nitrophenyl)amino]-3-oxopropanoate, 13.7 grams (99.1 mmol) of anhydrous potassium carbonate, 40 milliliters of anhydrous dimethylformamide and 3.4 milliliters (40.0 mmol) of 1,2-dibromoethane were reacted for a period of 7 days to give 1.6 grams (5.8 mmol) of ethyl 1-(4-nitrophenylaminocarbonyl)cyclopropanecarboxylate as a pale yellow solid having a melting point of 159.0° C.-161.0° C. The total yield was 15 percent. Recrystallization from methylene chloride-hexane furnished 1.39 grams (5.0 mmol) of 1-(4-nitrophenylaminocarbonyl)cyclopropanecarboxylate as pale yellow needles having a melting point of 159.5° C.-161.0° C. NMR analysis of the product indicated the following:

'H NMR (CDCl$_3$) δ11.78 (1H, bs), 8.35 (2H, d, J=9 Hz ), 7.85 (2H, d, J=9 Hz ), 4.27 (2H, q, J=7 Hz), 1.6-2.2 (4H, m), 1.28 (3H, t, J=7 Hz) ppm.

Other fractions eluted contained 1.51 grams (5.4 mmol) of N-(4-nitrophenyl)-2-carboethoxy-γ-butyrolactam as a pale yellow solid having a melting point of 51° C.-55° C. NMR analysis indicated the following:

'H NMR (CDCl$_3$)δ8.38 (2H, d, J=10 Hz), 7.95 (2H, d, J=10 Hz), 4.33 (2H, q, J=7 Hz), 3.5-4.3 (3H, m), 2.3-2.8 (2H, m), 1.33 (3H, t, J=7 Hz) ppm.

EXAMPLE 1

Preparation of ethyl 1-(4-bromo-2-methylphenylaminocarbonyl)cyclopropanecarboxylate Into a 500 milliliter three-necked Morton flask equipped with a mechanical stirrer, thermometer and nitrogen inlet and outlet was added 30.0 grams (0.10 mol) of ethyl 3-[4-bromo-2-methylphenyl)amino]-3-oxopropanoate prepared as in Example A, 34.5 grams (0.25 mol) of finely ground anhydrous potassium carbonate, 100 milliliters of dry dimethylformamide and 8.60 milliliters (0.10 mol) of 1,2-dibromoethane. The resulting mixture was stirred vigorously at ambient temperature under a nitrogen atmosphere for a period of 55 hours. During the first hour, the reaction exothermed from a temperature of 24° C. to 37° C. and, after 2 hours, high pressure liquid chromatographic analysis showed the reaction to be about 70 percent complete. The product was isolated by diluting with methylene chloride, filtering off the solids and concentrating under reduced pressure to give a yellow solid. Chromatography on silica gel with a 3:1 volume/volume hexane-ethyl acetate eluent provided ethyl 1-(4-bromo-2-methylphenylaminocarbonyl)cyclopropanecarboxylate in two portions: 0.6 grams (1.8 mmol) of a pale yellow solid having a melting point of 89.5° C.-90.0° C. and 24.8 grams (0.076 mol) of a colorless solid having a melting point of 90.0° C.-90.5° C. The total yield was 81.0 percent based on a 96.7 weight percent assay of the starting ethyl 3-[(4-bromo-2-methylphenyl)amino]-3-oxopropanoate. NMR analysis of the product indicated the following:

'H NMR (CDCl$_3$) δ10.93 (1H, bs), 8.13 (2H, d, J=9 Hz ), 7.2-7.5 (2H, m), 4.30 (2H, q, J=7 Hz ), 2.45 (3H, s), 1.6-2.1 (4H, m), 1.40 (3H, J=7 Hz)ppm.

EXAMPLE 2

Preparation of ethyl 1-(4-bromo-2-methylphenylaminocarbonyl)cyclopropanecarboxylate Into a 250 milliliter three-necked round-bottom reaction flask equipped with a mechanical stirrer, thermometer and nitrogen inlet and outlet was added 5.0 grams (17.0 mmol) of ethyl 3-[(4-bromo-2-methylphenyl)amino]-3-oxopropanoate prepared as in Example A, 5.73 grams (42.0 mmol) of anhydrous potassium carbonate, 20 milliliters of anhydrous dimethylformamide and 1.7 milliliters (20.0 mol) of 1,2-dibromoethane. The resulting mixture was stirred at ambient temperature under a nitrogen atmosphere and irradiated with ultra sound waves using a Bransonic 52 ultrasonic cleaning bath for a period of 4.25 hours. Ice was added to maintain the temperature of the bath between 26° C. and 31° C. After this period, high pressure liquid chromatographic analysis showed the reaction to be complete. The product was isolated by diluting with methylene chloride, filtering off the solids and concentrating under reduced pressure to give a yellow solid. Chromatography on silica gel with a 3:1 volume/volume hexane-ethyl acetate eluent provided 4.58 grams (14.0 mmol) of ethyl 1-(4-bromo-2-methylphenylaminocarbonyl)cyclopropanecarboxylate as a pale yellow solid having a melting point of 87° C.-89° C. The total yield was 87 percent based on a 96.7 weight percent assay of the starting ethyl 3-[(4-bromo-2-methylphenyl)amino]-3-oxopropanoate. NMR analysis of the product indicated the following:

'H NMR (CDCl$_3$) δ11.13 (1H, bs), 8.10 (2H, d, J=9 Hz), 7.3-7.7 (2H, m), 4.27 (2H, q, J=7 Hz), 2.37 (3H, s), 1.5-2.1 (4H, m), 1.25 (3H, J=7 Hz)ppm.

EXAMPLE 3

Preparation of ethyl 1-(4-bromo-2-methylphenylaminocarbonyl)cyclopropanecarboxylate Into a 300 milliliter three-necked round-bottom reaction flask equipped with a mechanical stirrer, thermometer and nitrogen inlet and outlet was added 5.0 grams (17.0 mmol) of ethyl 3-[(4-bromo-2-methylphenyl)amino]-3-oxopropanoate prepared as in Example A, 0.30 grams (0.83 mmol) of dibenzo-18-crown-6 ether, 1.4 milliliters (17.0 mmol) of 1,2-dibromoethane, 5.73 grams (42.0 mmol) of anhydrous potassium carbonate and 40 milliliters of acetonitrile. The resulting mixture was stirred at ambient temperature under a nitrogen atmosphere for a period of 5 days after which an additional 1.4 milliliters (17.0 mmol) of 1,2-dibromoethane was added and stirring then continued for an additional 3 days. The reaction was monitored throughout by high pressure liquid chromatography. After the stirring period, the mixture was filtered to remove solids which were then washed with methylene chloride, and the filtrate was evaporated to give 10.9 grams of an orange solid. Flash chromatography using 85:15 volume/volume hexane-ethyl acetate as the eluent provided 4.53 grams (13.9 mmol) of ethyl 1-(4-bromo-2-methylphenylaminocarbonyl)cyclopropanecarboxylate as a white solid having a melting point of 88.5° C.-90.0° C. The total yield was 86 percent based on a 96.7 weight percent assay of the starting ethyl 3-[(4-bromo-2-methylphenyl)amino]-3-oxopropanoate. NMR analysis of the product indicated the following:

'NMR (CDCl$_3$) δ11.23 (1H, bs), 8.13 (2H, d, J=9 Hz), 7.2-7.6 (2H, m), 4.28 (2H, q, J=7 Hz), 2.38 (3H, s), 1.5-2.0 (4H, m), 1.27 (3H, J=7 Hz)ppm.

EXAMPLE 4

Preparation of ethyl 1-(4-bromo-2-methylphenylaminocarbonyl)cyclopropanecarboxylate Into a 100 milliliter three-necked round-bottom reaction flask equipped with a mechanical stirrer, thermometer and nitrogen inlet and outlet was added 5.0 grams (17.0 mmol) of ethyl 3-[(4-bromo-2-methylphenyl)amino]-3-oxopropanoate prepared as in Example A, 1.7 milliliters (20.0 mmol) of 1,2-dibromoethane and 0.33 grams (0.83 mmol) of Aliquat ® 336 in 25 milliliters of methylene chloride. The resulting solution was stirred at ambient temperature under a nitrogen atmosphere as 0.2 milliliters of water and 4.60 grams (33.0 mmol) of potassium carbonate was added to the reaction flask. The resulting mixture was stirred for a total of 8 days and the reaction was monitored by high pressure liquid chromatography throughout this period (after one day, an additional 0.2 milliliters of water was added and, after 2 days, an additional 0.33 grams (0.83 mmol) of Aliquat ® 336 and 1.7 milliliters (20.0 mmol) of 1,2-dibromoethane were added). After the 8 day reaction period, the reaction mixture was diluted with 125 milliliters of water and extracted with methylene chloride. The combined organic extracts were washed with 125 milliliters of 3N aqueous HCl and 125 milliliters of saturated aqueous sodium bicarbonate. After drying over anhydrous magnesium sulfate and evaporation, a yellow solid residue was obtained which was flash chromatographed on silica gel with an 85:15 volume/volume hexane-ethyl acetate eluent to give 4.20 grams (12.9 mmol) of ethyl 1-(4-bromo-2-methylphenylaminocarbonyl)cyclopropanecarboxylate as a pale yellow solid having a melting point of 87.5° C.–89.0° C. The total yield was 80 percent based on a 96.7 weight percent assay of the starting ethyl 3-[(4-bromo-2-methylphenyl)amino]-3-oxopropanoate. NMR analysis of the product indicated the following:

$^1$H NMR (CDCl$_3$) δ11.25 (1H, bs), 8.08 (2H, d, J=9 Hz), 7.2–7.5 (2H, m), 4.22 (2H, q, J=7 Hz), 2.33 (3H, s), 1.4–2.1 (4H, m), 1.23 (3H, J=7 Hz)ppm.

EXAMPLE 5

Preparation of ethyl 1-(4-bromo-2-methylphenylaminocarbonyl)cyclopropanecarboxylate Into a 100 milliliter round-bottom reaction flask equipped with a magnetic stirrer and nitrogen inlet and outlet was added 3.0 grams (10.0 mmol) of ethyl 3-[(4-bromo-2-methylphenyl)amino]-3-oxopropanoate prepared as in Example A, 3.5 grams (25.0 mmol) of anhydrous potassium carbonate, 50 milliliters of dimethyl sulfoxide and 2.0 grams (10.0 mmol) of 2-bromoethyl ethyl carbonate. The resulting mixture was stirred at ambient temperature under a nitrogen atmosphere for a period of 3 days. The reaction mixture was then poured into an ice/water bath, extracted into ethyl ether and the ether extracts were dried over anhydrous magnesium sulfate. Concentration under reduced pressure gave 3.5 grams of a pale yellow solid which was chromatographed on silica gel (4:1 volume/volume hexaneethyl acetate) to separate 2.2 grams (6.7 mmol) of ethyl 1-(4-bromo-2-methyl-phenylaminocarbonyl)cyclopropanecarboxylate as a very pale yellow solid having a melting point of 86.0° C.–89.0° C. The total yield was 69 percent based on a 96.7 weight percent assay of the starting ethyl 3-[(4-bromo-2-methylpenyl)amino]-3-oxopropanoate. NMR analysis of the product indicated the following:

$^1$H NMR (CDCl$_3$) δ8.08 (2H, d, J=9 Hz), 7.2–7.6 (2H, m), 4.23 (2H, q, J=7 Hz), 2.35 (3H, s), 1.4–2.0 (4H, m), 1.28 (3H, J=7 Hz)ppm.

EXAMPLE 6

Preparation of ethyl 1-(4-bromo-2-methylphenylaminocarbonyl)cyclopropanecarboxylate Into a 50 milliliter three-necked Morton flask equipped with a mechanical stirrer, thermometer, condenser and nitrogen inlet and outlet was added 7.5 grams (25.0 mmol) of ethyl-3-[(4-bromo-2-methylphenyl)amino]-3-oxopropanoate prepared as in Example A and 10 milliliters of dimethyl sulfoxide. This solution was stirred under a nitrogen atmosphere and warmed to a temperature of 40° C. after which 5.4 grams (28.0 mmol) of 2-bromoethyl ethyl carbonate was added via a syringe pump over a 7 hour period. During the course of this addition, 8.6 grams (63.0 mmol) of anhydrous potassium carbonate was added portionwise. The mixture was stirred for a period of about 18 hours and then an additional 0.98 grams (5.0 mmol) of 2-bromoethyl ethyl carbonate was added. After an additional 8 hour reaction period, the mixture was poured onto ice and partitioned with ethyl ether. The ethereal extracts were dried over anhydrous magnesium sulfate and concentrated under reduced pressure to give 8.8 grams of a yellow solid which was chromatographed on silica gel (4:1 volume/volume hexane-ethyl acetate) to give 5.2 grams (15.9 mmol) of ethyl 1-(4-bromo-2-methylphenylaminocarbonyl)cyclopropanecarboxylate as a colorless solid having a melting point of 89.0° C.–90.5° C. The total yield was 66 percent based on a 96.7 weight percent assay of the starting ethyl 3-[(4-bromo-2-methylphenyl)amino]-3-oxopropanoate. NMR analysis of the product indicated the following:

$^1$H NMR (CDCl$_3$) δ8.00 (2H, d, J=9 Hz), 7.1–7.5 (2H, m), 4.20 (2H, q, J=7 Hz), 2.45 (3H, s), 1.5–2.0 (4H, m), 1.27 (3H, J=7 Hz)ppm.

EXAMPLE 7

Preparation of 1-(4-bromo-2-methylphenylaminocarbonyl)cyclopropanecarboxylic acid Into a 250 milliliter Erlenmeyer flask equipped with a magnetic stirrer and condenser was added 15.0 grams (0.05 mol) of ethyl 3-[(4-bromo-2-methylphenyl)amino]-3-oxopropanoate, 150 milliliters of dimethylformamide and 14.0 grams (0.10 mol) of 1-bromo-2-chloroethane. The resulting mixture was stirred at ambient temperature and potassium carbonate (4.0 grams, 0.03 mol) was added at a rate of 1 gram every 30 minutes. After liquid chromatographic analysis showed the ethyl 3-[(4-bromo-2-methylphenyl)amino]-3-oxopropanoate peak disappeared, potassium hydroxide (5.0 grams, 0.09 mol) was added until no ethyl 1-(4-bromo-2-methylphenylaminocarbonyl)cyclopropanecarboxylate remained. The reaction mixture was diluted to 300 milliliters with water and acidified with concentrated HCl to a pH of 1 to afford a solid material. The solid was collected on a Buchner funnel and dried under ambient temperature to give 13.65 grams (0.046 mol) of 1-(4-bromo-2-methylphenylaminocarbonyl)cyclopropanecarboxylic acid. The total yield was 91.5 percent based on a 97.6 weight percent liquid chromatographic assay of the starting ethyl 3-[(4-bromo-2-methylphenyl)amino]-3-oxopropanoate.

EXAMPLE 8

Preparation of 1-(4-bromo-2-methylphenylaminocarbonyl)cyclopropanecarboxylic acid Into a 250 milliliter Erlenmeyer flask equipped with a magnetic stirrer was added 15.0 grams (0.05 mol) of ethyl 3-[(4-bromo-2-methylphenyl)amino]-3-oxopropanoate prepared as in Example A, 16.56 grams (0.12 mol) of potassium carbonate, 150 milliliters of dimethylformamide and 5.16 milliliters (0.06 mol) of 1,2-dibromethane. The resulting mixture was stirred at ambient temperature for a period of 23 hours (liquid chromatographic analysis indicated 87 percent and 95 percent conversions after 2 and 6 hours respectively). Potassium hydroxide (4.0 grams, 0.07 mol) was then added in one gram increments until no ethyl 1-[(4-bromo-2-methylphenylaminocarbonyl)cyclopropanecarboxylate remained. The reaction mixture was diluted to 900 milliliters with water and acidified with concentrated HCl to a pH of 1–2 to afford a yellow percipitate. The yellow precipitate was dried for a period of about 18 hours in an unheated vacuum oven to give 11.88 gram (0.04 mol) of 1-(4-bromo-2-methylpheylaminocarbonyl)cyclopropanecarboxylic acid. The total yield was 80 percent based on a 96.7 weight percent liquid chromatographic assay of the starting ethyl 3-[(4-bromo-2-methylphenyl)amino]-3-oxopropanoate.

EXAMPLE 9

Preparation of ethyl 1-(2,4-dichlorophenylaminocarabonyl)cyclopropanecarboxylate In a manner similar to the procedure described in Example B except that a one liter three-necked Morton flask was used, 39.0 grams (0.14 mol) of ethyl 3-[(2,4-dichlorophenyl)amino]-3-oxopropanoate, 53.9 grams (0.39 mol) of anhydrous potassium carbonate, 125 milliliters of anhydrous dimethylformamide and 13.4 milliliters (0.16 mol) of 1,2-dibromoethane were reacted for a period of 65 hours to give 35.3 grams (0.117 mol) of ethyl 1-(2,4-dichlorophenylaminocarbonyl)cyclopropanecarboxylate as a pale yellow solid having a melting point of 95.0° C.–96.0° C. The total yield was 83 percent. NMR analysis of the product indicated the following:

$^1$H NMR (CDCl$_3$) δ11.33 (1H, bs), 8.32 (1H, d, J=8 Hz), 7.37 (1H, d, J=2 Hz), 7.17 (1H, dd, J=2, 8 Hz), 4.20 (2H, q, J=7 Hz), 1.5–2.0 (4H, m), 1.25 (3H, t, J=7 Hz)ppm.

EXAMPLE 10

Preparation of ethyl 1-(4-methoxy-2-methylphenylaminocarbonyl)cyclopropanecarboxylate In a manner similar to the procedure described in Example B except that a 100 milliliter three-necked Morton flask was used, 9.05 grams (35.8 mmol) of ethyl 3-[(4-methoxy-2-methylphenyl)amino]-3-oxopropanoate, 12.05 grams (87.3 mmol) of anhydrous potassium carbonate, 35 milliliters of anhydrous dimethylformamide and 3.5 mmol) of 1,2-dibromoethane were reacted for a period of 3 days to give 7.7 grams (28.0 mmol) of 1-(4-methoxy-2-methylphenylaminocarbonyl)cyclopropanecarboxylate as a colorless solid having a melting point of 84.0° C.–84.5° C. The total yield was 78 percent. NMR analysis of the product indicated the following:

$^1$H NMR (CDCl$_3$) δ10.93 (1H, bs), 7.95 (1H, d, J=10 Hz), 6.6–7.0 (2H, m) 4.27 (2H, q, J=7 Hz), 3.85 (3H, s), 2.37 (3H, s), 1.4–2.0 (4H, m), 1.27 (3H, t, J=7 Hz)ppm.

The other fractions eluted contained 0.4 grams (1.4 mmol) of N-(2-methyl-4-methoxyphenyl)-2-carboethoxy-γ-butyrolactam as a pale yellow oil. NMR analysis indicated the following:

$^1$H NMR (CDCl$_3$) δ7.18 (1H, dd, J=2, 8 Hz), 6.7–7.0 (2H, m), 4.32 (2H, q, J=7 Hz), 3.3–4.1 (3H, m with a 3H, s at 3.85), 2.55 (2H, t, J=7 Hz), 2.23 (3H, s), 1.32 (3H, t, J=7 Hz)ppm.

EXAMPLE 11

Preparation of ethyl 1-(4-nitro-2-methylphenylaminocarbonyl)cyclopropanecarboxylate In a manner similar to the procedure described in Example B except that a 250 milliliter three-necked round-bottom flask was used, 8.0 grams (30.0 mmol) of ethyl 3-[(4-nitro-2-methylphenyl)amino]-3-oxopropanoate, 10.35 grams (75.0 mmol) of anhydrous potassium carbonate, 2.6 milliliters (30.0 mmol) of 1,2-dibromoethane and 40 milliliters of anhydrous dimethylformamide were reacted for a period of 7 days to give, after flash chromatography with 85:15 volume/volume hexane-ethyl acetate eluent, 6.52 grams (22.3 mmol) of ethyl 1-(4-nitro-2-methylphenylaminocarbonyl)cyclopropanecarboxylate as a pale yellow solid having a melting point of 140° C.–147° C. The total yield was 74 percent. An analytical sample was prepared by recrystallization from hexane-methylene chloride to give 5.15 grams (17.6 mmol) of ethyl 1-(4-nitro-2-methylphenylaminocarbonyl)cyclopropanecarboxylate as pale yellow needles having a melting point of 144.5° C.–147° C. NMR analysis of the product indicated the following:

$^1$H NMR (CDCl$_3$) δ11.70 (1H, bs), 8.58 (1H, d, J=10 Hz), 8.0–8.4 (2H, m), 4.23 (2H, q, J=7 Hz), 2.52 (3H, s), 1.6–2.0 (4H, m), 1.30 (2H, t, J=7 Hz)ppm.

Other fractions eluted contained 0.27 grams (0.67 mmol) of N-(2-methyl-4-nitrophenyl)-2-(2-bromoethyl)-2-carboethoxy-γ-butyrolactam as a yellow liquid. NMR analysis indicated the following:

$^1$H NMR (CDCl$_3$) δ7.8–8.3 (2H, m) 7.32 (1H, dd, J=2, 7 Hz), 4.28 (2H, q, J=7 Hz), 3.3–3.9 (4H, m), 2.1–3.0 (4H, m), 2.32 (3H, s), 1.32 (3H, t, J=7 Hz)ppm.

Other fractions eluted contained 0.14 grams (0.48 mmol) of N-(2-methyl-4-nitrophenyl)-2-carboethoxy-γ-butyrolactam as a yellow liquid. NMR analysis indicated the following:

$^1$H NMR (CDCl$_3$) δ8.0–8.5 (2H, m), 7.45 (1H, dd, J=2, 8 Hz), 4.35 (2H, q, J=7 Hz), 3.4–4.2 (3H, m), 2.1–2.9 (2H, m), 2.38 (3H, s), 1.33 (3H, t, J=7 Hz)ppm.

EXAMPLE 12

Preparation of ethyl 1-(4-chloro-2-fluorophenylaminocarbonyl)cyclopropanecarboxylate In a manner similar to the procedure described in Example B, 31.0 grams (119.0 mmol) of ethyl 3-[(4-chloro-2-fluorophenyl)amino]-3-oxopropanoate, 41.4 grams (300.0 mmol) of anhydrous potassium carbonate, 100 milliliters anhydrous dimethylformamide and 10.4 milliliters (120.0 mmol) of 1,2-dibromoethane were reacted for a period of 3 days to give 20.6 grams (72.0 mmol) of ethyl 1-(4-chloro-2-fluorophenylaminocarbonyl)cyclopropanecarboxylate as a colorless solid having a melting point of 94.0° C.–95.5° C. The total yield was 61 percent. NMR analysis of the product indicated the following:

$^1$H NMR (CDCl$_3$) δ11.17 (1H, bs), 8.28 (1H, dd, J=9, 9 Hz), 6.93–7.30 (2H, m), 4.22 (2H, q, J=7 H), 1.50–2.00 (4H, m), 1.27 (3H, t, J=7 Hz)ppm.

EXAMPLE 13

Preparation of ethyl 1-(4-bromo-2-methylphenylaminocarbonyl)cyclopropanecarboxylate Into a 500 milliliter three-necked round-bottom reaction flask equipped with a mechanical stirrer, thermometer, nitrogen inlet and outlet and oil bath was added 30.0 grams (0.10 mol) of ethyl 3-[(4-bromo-2-methylphenyl)amino]-3-oxopropanoate prepared as in Example A, 34.5 grams (0.25 mol) of anhydrous potassium carbonate, 100 milliliters of anhydrous dimethylformamide and 8.6 milliliters (0.10 mol) of 1,2-dibromoethane. The resulting mixture as stirred under a nitrogen atmosphere at a temperature of 65° C. for a period of 3 hours and then at a temperature of 80° C. for a period of 3.5 hours. Following this period, high pressure liquid chromatographic analysis showed the reaction to be incomplete. An additional 13.8 grams (0.10 mol) of anhydrous potassium carbonate was added and the reaction mixture was stirred at ambient temperature for a period of 16 hours. An additional 1.7 milliliters (0.02 mol) of 1,2-dibromoethane was then added and the reaction mixture was heated at a temperature of 75° C. for a period of 3.5 hours. Anhydrous potassium carbonate (6.0 grams, 0.043 mol) was then added and heating was continued for an additional 2.5 hours. The reaction mixture was then cooled, diluted with methylene chloride and filtered to remove suspended solids. Concentration under reduced pressure gave a brown liquid which was chromatographed on silica gel using 3:1 volume/volume hexane-ethyl acetate as the eluent. Early fractions contained 17.8 grams (55.0 mmol) of 1-(4-bromo-2-methylphenylaminocabonyl)cyclopropanecarboxylate as a pale yellow solid having a melting point of 87.0° C.–90.0° C. The total yield was 56.0 percent based on a 96.7 weight percent assay of the starting ethyl 3-[(4-bromo-2-methylphenyl)amino]-3-oxopropanoate. NMR analysis of the product indicated the following:

$^1$H NMR (CDCl$_3$) δ11.17 (1H, bs), 8.13 (2H, d, J=9 Hz), 7.2–7.6 (2H, m), 4.23 (2H, q, J=7 Hz), 2.37 (3H, s), 1.5–2.0 (4H, m), 1.23 (3H, J=7 Hz)ppm.

EXAMPLE 14

Preparation of ethyl 1-(4-bromo-2-methylphenylaminocarbonyl)cyclopropanecarboxylate Into a 50 milliliter three-necked round-bottom reaction flask equipped with a mechanical stirrer, thermometer and nitrogen inlet and outlet was added 5.0 grams (17.0 mmol) of ethyl 3-[(4-bromo-2-methylphenyl)amino]-3-oxopropanoate, 3.91 grams (16.7 mmol) of 2-chloroethyl-paratoluenesulfonate, 5.74 grams (41.6 mmol) of anhydrous potassium carbonate and 17 milliliters of anhydrous dimethylformamide. The resulting mixture was stirred at ambient temperature under a nitrogen atmosphere for a period of 4 days. The product was then isolated by diluting with methylene chloride, filtering off the solids and concentrating under reduced pressure to give a solid material. Chromatography on silica gel with a 3:1 volume/volume hexane-ethyl acetate eluent provided 1.89 grams (5.8 mmol) of ethyl 1-(4-bromo-2-methylphenylaminocarbonyl)cyclopropanecarboxylate as a white solid having a melting point of 87.5° C.–89.0° C. The total yield was 35 percent based on a 96.7 weight percent assay of the staring ethyl 3-[(4-bromo-2-methylphenyl)amino]-3-oxopropanoate. NMR analysis of the product indicated the following:

$^1$H NMR (CDCl$_3$) δ11.25 (1H, bs), 8.10 (2H, d, J=9 Hz), 7.3–7.7 (2H, m), 4.30 (2H, q, J=7 Hz), 2.38 (3H, s), 1.5–2.0 (4H, m), 1.27 (3H, J=7 Hz)ppm.

EXAMPLE 15

Preparation of ethyl 1-(4-bromo-2-methylphenylaminocarbonyl)cyclopropanecarboxylate Into a 25 milliliter three-necked round-bottom reaction flask equipped with a magnetic stirrer and nitrogen inlet and outlet was added 330 milligrams (1.1 mmol) of ethyl 3-[(4-bromo-2-methylphenyl)amino]-3-oxopropanoate prepared as in Example A, 350 milligrams (2.5 mmol) of anhydrous potassium carbonate, 2.0 milliliters of anhydrous dimethylformamide and 0.16 milliliters (2.0 mmol) of 1,2-dichloroethane. The resulting mixture was stirred at ambient temperature under a nitrogen atmosphere for a period of 84 hours. The reaction mixture was then diluted with methylene chloride, filtered to remove solids and concentrated under reduced pressure. Chromatography of the residue on silica gel using a 3:1 volume/volume hexane-ethyl acetate eluent furnished 110 milligrams (0.34 mmol) of ethyl (1-(4-bromo-2-methylphenylaminocarbonyl)cyclopropanecarboxylate as an off-white solid. The total yield was 31.0 percent based on a 96.7 weight percent assay of the starting ethyl 3-[(4-bromo-2-methylphenyl)amino]-3-oxopropanoate. NMR analysis of the product indicated the following:

$^1$H NMR (CDCl$_3$) δ8.00 (2H, d, J=9 Hz), 7.1–7.5 (2H, m), 4.20 (2H, q, J=7 Hz), 2.33 (3H, s), 1.5–1.9 (4H, m), 1.27 (3H, J=7 Hz)ppm.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

We claim:

1. A process for preparing a compound of formula (i)

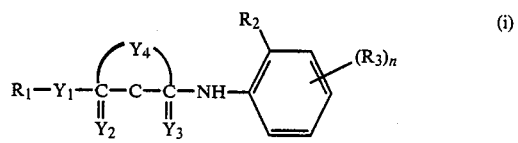

which comprises reacting a compound of formula (ii)

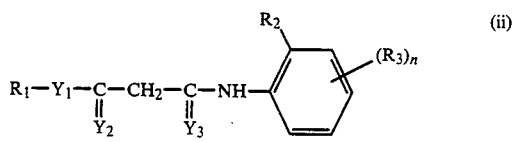

with a compound of formula (iii)

in the presence of a solvent and a base; wherein:
R$_1$ alkyl, hydroxyalkyl, alkoxyalkyl, alkoxycarbonylalkyl, alkylaminoalkyl, dialkylaminoalkyl, aryl, mercaptoalkyl, alkylthioalkyl, arylthioalkyl, aryloxyalkyl, alkylsulfonylalkyl, alkylsulfinylalkyl, acylalkyl, aroylalkyl, dialkoxyphosphinylalkyl, diaryloxyphosphinylalkyl, hydroxyalkylthioalkyl, hydroxyalkylsulfonylalkyl, alkoxyalkylthioalkyl, alkoxyalkylsulfonylalkyl, poly(oxyalkylene)alkyl, cyanoalkyl, nitroalkyl, alkylideneamino, carbamoylalkyl, alkylcarbamoylalkyl, dialkylcarbamoylalkyl, aminoalkyl, acylaminoalkyl, acyloxyalkyl, alkoxycarbonylaminoalkyl, cyanoaminoalkyl, carbamoyloxyalkyl, alkylcarbamoyloxyalkyl, dialkylcarbamoyloxyalkyl, aminosulfonylalkyl, alkylaminosulfonylalkyl or dialkylaminosulfonylalkyl;

$R_2$ and $R_3$ are the same or different and are halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonyl amino, acyloxy or alkenyl;

n is a value of from 0 to 4;

$Y_1$ is O, S or N(alkyl);

$Y_2$ and $Y_3$ are independently oxygen or sulfur;

$Y_4$ is a substituted or unsubstituted branched or straight chain containing two or more carbon atoms or heteroatoms in any combination in which the permissible substituents are the same or different and are one or more halogen, haloalkyl, polyhaloalkyl, polyhaloalkoxy, alkyl, alkoxy, alkylthio, alkylsulfonyl, alkylsulfinyl, aryl, aryloxy, arylthio, arylsulfonyl, nitro, cyano, dialkoxyphosphinyl, acyl, aroyl, alkoxycarbonyl, alkoxycarbonylalkyl, acylamino, sulfonylamino, alkylsulfonylamino, acyloxy or alkenyl, with the proviso that $X_1$ and $X_2$ are not directly bonded to a heteroatom; and $X_1$ and $X_2$ are independently nucleofuge groups having sufficient leaving capability to permit the reaction of a compound of formula (iii) with a compound of formula (ii) to form a compound of formula (i).

2. The process of claim 1 in which the molar ratio of the compound of formula (ii) to the compound of formula (iii) is from about 0.25:1 to about 1.5:1.

3. The process of claim 1 in which the compound of formula (ii) is ethyl 3-[(4-bromo-2-methylphenyl)amino]-3-oxopropanoate.

4. The process of claim 1 in which the compound of formula (iii) is selected from 1,2-dibromoethane, 1-bromo-2-chloroethane and 2-bromoethyl ethyl carbonate.

5. The process of claim 1 in which the compound of formula (iii) is 1,2-dibromoethane.

6. The process of claim 1 in which the solvent is a polar aprotic solvent.

7. The process of claim 6 in which the solvent is selected from dimethylformamide, dimethylsulfoxide, tetramethylenesulfone and dimethylacetamide.

8. The process of claim 1 in which the solvent is dimethylformamide.

9. The process of claim 1 in which the base is an alkali metal carbonate or an alkaline earth metal carbonate.

10. The process of claim 9 in which the base is potassium carbonate.

11. The process of claim 1 in which the base has a particle size of from about 10 microns to about 1000 microns in diameter.

12. The process of claim 1 in which the reaction temperature is from about 20° C. to about 75° C.

13. The process of claim 1 in which the reaction is carried out in the presence of ultrasonic irradiation.

14. The process of claim 1 which is a liquid-liquid phase transfer system containing water, an immiscible solvent and a phase transfer catalyst.

15. The process of claim 1 which is a solid-liquid phase transfer system containing an organic solvent and a phase transfer catalyst.

16. The process of claim 1 in which the compound of formula (i) has the following formula:

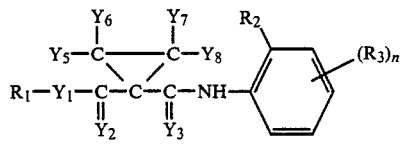

wherein $R_1$, $R_2$, $R_3$, n, $Y_1$, $Y_2$ and $Y_3$ are as defined in claim 1 and $Y_5$, $Y_6$, $Y_7$ and $Y_8$ are independently hydrogen, halogen or alkyl.

17. The process of claim 1 in which the compound of formula (i) has the following formula:

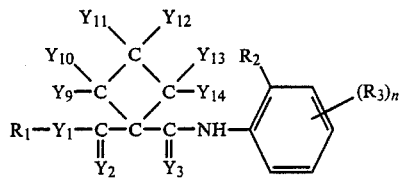

wherein $R_1$, $R_2$, $R_3$, n, $Y_1$, $Y_2$ and $Y_3$ are as defined in claim 1 and $Y_9$, $Y_{10}$, $Y_{11}$, $Y_{12}$, $Y_{13}$ and $Y_{14}$ are independently hydrogen, halogen or alkyl.

18. The process of claim 1 in which the compound of formula (i) is ethyl 1-(4-bromo-2-methylphenylaminocarbonyl)cyclopropanecarboxylate.

19. The process of claim 1 which further comprises reacting the compound of formula (i) with an alkali metal hydroxide to form an alkali metal salt derivative thereof.

20. The process of claim 19 in which the alkali metal salt derivative is the sodium salt or potassium salt of ethyl 1-(4-bromo-2-methylphenylaminocarbonyl)cyclopropanecarboxylate.

21. The process of claim 19 which further comprises reacting the alkali metal salt derivative with a mineral acid to form an acid derivative thereof.

22. The process of claim 21 in which the acid derivative is 1-(4-bromo-2-methylphenylaminocarbonyl)cyclopropanecarboxylic acid.

23. The process of claim 21 which further comprises reacting the acid derivative with ammonia or an amine to form an amine salt thereof.

24. The process of claim 1 in which the reaction period is from about 4 hours to about 10 hours.

25. The process of claim 1 in which an antifoaming agent is added to the reaction.

26. The process of claim 25 in which the antifoaming agent is added in an amount of from about 0.0001 weight percent to about 1.0 weight percent based on the total weight of the reaction mass.

27. The process of claim 1 in which a surfactant is added to the reaction.

28. The process of claim 27 in which the surfactant is added in an amount of from about 0.0001 weight percent to about 1.0 weight percent based on the total weight of the reaction mass.

29. The process of claim 1, wherein $X_1$ and $X_2$ are independently selected from halogen, alkoxycarbonyloxy, haloalkylcarbonyloxy, polyhaloalkylcarbonyloxy, arylsulfonyloxy, alkylsulfonyloxy, haloalkylsulfonyloxy, polyhaloalkylsulfonyloxy, halosulfonyloxy, nitrooxy, dialkoxyphosphinyloxy, or diaryloxyphosphinyloxy, aryloxy, or dialkylsulfonium, trialkylammonium or dialkyloxonium salts.

30. The process of claim 1, wherein for the compound of formula (iii), at least one of $X_1$ and $X_2$ is bromo or iodo.

31. The process of claim 6 in which the solvent is selected from N-methyl pyrrolidinone, hexamethylphosphoric triamide and 3-methyl-2-oxazolidinone.

32. The process of claim 1, wherein the solvent is selected from acetonitrile, tetrahydrofuran, acetone, dioxane, diethyl ether, toluene, benzene, methanol, ethanol and 1,2-dibromoethane.

33. The process of claim 12, in which the reaction temperature is from about 25° C. to about 50° C.

* * * * *

UNITED STATES PATENT AND TRADEMARK OFFICE
CERTIFICATE OF CORRECTION

PATENT NO. : 4,736,056
DATED : April 5, 1988
INVENTOR(S) : SMITH et al.

It is certified that error appears in the above-identified patent and that said Letters Patent is hereby corrected as shown below:

In the Specification

Column 1, line 40, in formula (i)

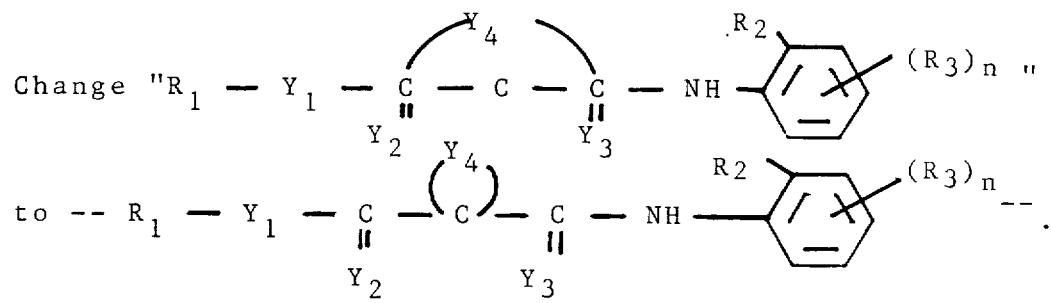

Column 2, line 5, in formula (i)

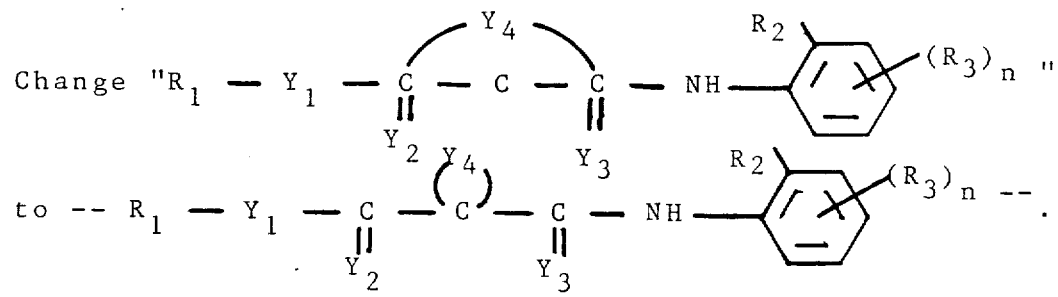

UNITED STATES PATENT AND TRADEMARK OFFICE
CERTIFICATE OF CORRECTION

PATENT NO. : 4,736,056

DATED : April 5, 1988

INVENTOR(S) : SMITH et al.

It is certified that error appears in the above-identified patent and that said Letters Patent is hereby corrected as shown below:

Column 6, line 52, change "deriviatives" to -- derivatives --.

Column 9, line 13, after "22.0" change "mol" to -- mmol --.

Column 15, line 16, change "pheylaminocarbonyl" to -- phenylaminocarbonyl --.

Column 16, line 67, after " = ", change "7 H" to -- 7 Hz --.

Column 18, line 27, after "ethyl" change "(1-(4-bromo" to -- 1-(4-bromo--.

UNITED STATES PATENT AND TRADEMARK OFFICE
CERTIFICATE OF CORRECTION

PATENT NO.  : 4,736,056
DATED       : April 5, 1988
INVENTOR(S) : SMITH et al.

It is certified that error appears in the above-identified patent and that said Letters Patent is hereby corrected as shown below:

Claim 1, line 2, in formula i, change

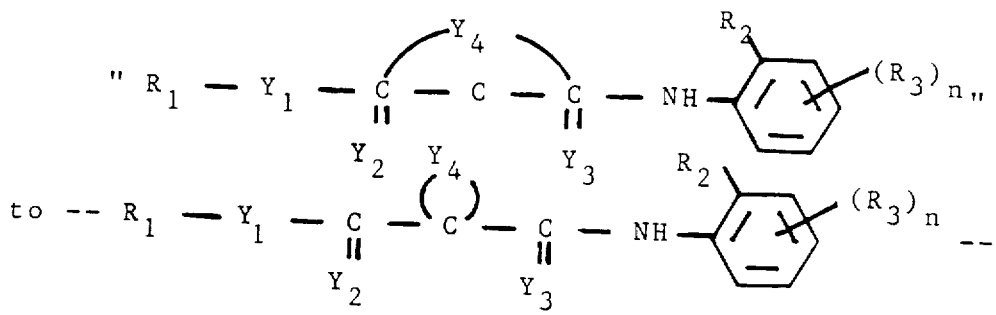

line 8, after "$R_1$", insert -- is --.

Signed and Sealed this

Sixth Day of February, 1990

Attest:

JEFFREY M. SAMUELS

Attesting Officer    Acting Commissioner of Patents and Trademarks